US012169202B2

(12) United States Patent
Emmett et al.

(10) Patent No.: US 12,169,202 B2
(45) Date of Patent: Dec. 17, 2024

(54) MEASUREMENT OF 2-HYDROXYGLUTARATE ENANTIOMER LEVELS AS A BIOMARKER FOR IDH MUTANT CANCERS

(71) Applicant: Board of Regents, The University of Texas System, Austin, TX (US)

(72) Inventors: Mark R. Emmett, Galveston, TX (US); Shinji K. Strain, Texas City, TX (US); Morris D. Groves, West Lake Hills, TX (US)

(73) Assignee: Board of Regents, The University of Texas System, Austin, TX (US)

( * ) Notice: Subject to any disclaimer, the term of this patent is extended or adjusted under 35 U.S.C. 154(b) by 470 days.

(21) Appl. No.: 17/172,940

(22) Filed: Feb. 10, 2021

(65) Prior Publication Data

US 2021/0263037 A1 Aug. 26, 2021

Related U.S. Application Data

(60) Provisional application No. 62/975,609, filed on Feb. 12, 2020.

(51) Int. Cl.
*G01N 33/48* (2006.01)
*G01N 33/574* (2006.01)

(52) U.S. Cl.
CPC .............................. *G01N 33/57488* (2013.01)

(58) Field of Classification Search
None
See application file for complete search history.

(56) References Cited

PUBLICATIONS

Strain et al. (2020) Clinical Mass Spectrometry 15: 16-24.*
Van Tellingend et al., "Overcoming the blood-brain tumor barrier for effective glioblastoma treatment", Elsevier, Drug Resistance Updates, 19 (2015) 1-12.
Wang, et al., "Prognostic significance of 2-hydroxyglutarate levels in acute myeloid leukemia in China", PNAS, Oct. 15, 2013, vol. 110, No. 42, 17017-17022.
Willekens et al., "Serum 2-Hydroxyglutarate Level Can Predict IDH2 Mutation in Myeloid Sarcoma", Gustave Roussy, Cancer Campus.
Wishart et al., "HMDB 4.0: the human metabolome database for 2018", D608-D617 Nucleic Acids Research, 2018, vol. 46, Database issue.
Wobbrock et al., "The Aligned Rank Transform for Nonparametric Factorial Analyses Using Only ANOVA Procedures", CHI 2011 • Session: Research Methods, May 7-12, 2011 • Vancouver, BC, Canada.
Worth et al., "Rotenone Stereospecifically Increases (S)-2-Hydroxyglutarate in SHSY5Y Neuronal Cells", Chemical Research in Toxicology, 2015, 28, 948-954.
Ye et al., "Metabolism, Activity, and Targeting of D-and L-2-Hydroxyglutarates", Trends in Cancer, Feb. 2018, vol. 4, No. 2.
Balss et al., "Pretreatment D-2-hydroxyglutarate serum levels negatively impact on outcome in IDH1-mutated acute myeloid leukemia", Leukemia, 2016, 30, 782-788.
Borger et al., "Circulating Oncometabolite 2-Hydroxyglutarate Is a Potential Surrogate Biomarker in Patients with socitrate Dehydrogenase-Mutant Intrahepatic Cholangiocarcinoma", Clinical Cancer Research, Jan. 29, 2014, 10.1158/1078-0432.
Bories et al., "Establishing assay-specific 97.5th percentile upper reference limit for serum D-2-hydroxyglutarate for the management of patients with acute myeloid leukemia", Clin Chem Lab Med, 2019,57 (4):e57-e59.
Brunner et al., "Acute Myeloid Leukemia: Biology, Cytogenetics and Molecular Markers in Diagnosis and Prognosis", Poster II, Dec. 3, 2015.
Calderon et al., "Chiral separation of 2-hydroxyglutaric acid on cinchonan carbamatebased weak chiral anion exchangers by high-performance liquidchromatography", Journal of Chromatography A, 1467, 2016, 239-245.
Calderon et al., "Chiral separation of short chain aliphatic hydroxycarboxylic acids oncinchonan carbamate-based weak chiral anion exchangers andzwitterionic chiral ion exchangers", Journal of Chromatography A, 1487, 2017, 194-200.
Capper et al., "2-Hydroxyglutarate concentration in serum from patients with gliomas does not correlate with IDH1/2 mutation status or tumor size", International Journal of Cancer, 131, 2012, 766-768.
Chalmers et al., "D-2-Hydroxyglutaric Aciduria: Case Report and Biochemical Studies", J. Inher. Metab. Dis. 3 (1980) 11-15.
Cheng et al., Sensitive Determination of Onco-metabolites of D- and L-2-hydroxyglutarate Enantiomers by Chiral Derivatization Combined with Liquid Chromatography/Mass Spectrometry Analysis, Scientific Reports, 5:15217 DOI: 10.1038/srep15217, 2015.
Churchill et al., "Discordant intracellular and plasma D-2-hydroxyglutarate levels in a patient with IDH2 mutated angioimmunoblastic T-cell lymphoma", Int J Clin Exp Pathol 2015;8(9):11753-11759.
Cohen et al., "IDH1 and IDH2 mutations in gliomas", Current Neurology and Neuroscience Reports, May 2013 DOI: 10.1007/s11910-013-0345-4—Source: PubMed Citations 303.
Dang et al, "Cancer-associated IDH1 mutations produce 2-hydroxyglutarate" vol. 462| Dec. 10, 2009| doi:10.1038/nature08617.
Delahousse et al., "Circulating oncometabolite D-2-hydroxyglutarate enantiomer is a surrogate marker of isocitrate dehydrogenaseemutated intrahepatic cholangiocarcinomas", European Journal of Cancer 90 (2018) 83-91.
Dinardo et al., "Serum 2-hydroxyglutarate levels predict isocitrate dehydrogenase mutations and clinical outcome in acute myeloid leukemia", Myeloid Neoplasia, Regular Article, Blood, Jun. 13, 2013, vol. 121, No. 24.

(Continued)

*Primary Examiner* — Michael D Pak
(74) *Attorney, Agent, or Firm* — Edwin S. Flores; Daniel J. Chalker; Chalker Flores, LLP

(57) ABSTRACT

The present invention includes a method of identifying 2-hydroxygluterate (2-hg) metabolites in a sample comprising: obtaining the sample from a patient; extracting the 2-hydroxygluterate (2-hg) metabolites from the sample without modifying a chiral center of the 2-hg metabolites; separating the one or more 2-hg metabolites in the sample using a chiral gas chromatography capillary column; and quantitating an amount of 2-hg metabolites in the sample using mass spectrometry.

4 Claims, 4 Drawing Sheets

(56) References Cited

PUBLICATIONS

Duran et al. "L-2-Hydroxyglutaric Aciduria: an Inborn Error of Metabolism?", J. Inher. Metab. Dis. 3 (1980) 109-112.

Eng et al., "ALDH2, ADH1B, and ADH1C Genotypes in Asians: a Literature Review", Alcohol Research & Health, vol. 30, No. 1, 2007.

FDA, "Bioanalytical Method Validation Guidance for Industry" May 2018, Biopharmaceutics.

Franceschi et al., "Chronic Inflammation (Inflammaging) and Its Potential Contribution to Age-Associated Diseases", Journals of Gerontology: Biological Sciences Cite journal as: J Gerontol A Biol Sci Med Sci Jun. 2014;69(S1): S4-S9, doi:10.1093/gerona/glu057.

Gibson et al., "Stable-Isotope Dilution Analysis of D- and L-2-Hydroxyglutaric Acid: Application to the Detection and Prenatal Diagnosis of D- and L-2-Hydroxyglutaric Acidemias", Pediatric Research, vol. 34. No. 3. 1993.

Gross et al, "Cancer-associated metabolite 2-hydroxyglutarate accumulates in acute myelogenous leukemia with socitrate dehydrogenase 1 and 2 mutations", Jem, J. Exp. Med. vol. 207 No. 2 339-344.

Han et al. "Elevated D-2-hydroxyglutarate during colitis drives progression to colorectal cancer", PNAS, Jan. 30, 2018, vol. 115, No. 5, 1057-1062.

Hoffmann et al., "Physiology and Pathophysiology of Organic Acids in Cerebrospinal Fluid", J. Inher. Metab. Dis. 16 (1993) 648-669.

Intlekofer et al, "Hypoxia Induces Production of L-2-Hydroxyglutarate", Cell Metabolism, 2015, Cell Metabolism 22, 304-311.

Janin et al., "Serum 2-Hydroxyglutarate Production in IDH1- and IDH2-Mutated De Novo Acute Myeloid Leukemia: A Study by the Acute Leukemia French Association Group", Journal of Clinical Oncology, vol. 32, No. 4, Feb. 1, 2014.

Jones et al., "Acute Myeloid Leukemia", Methods in Molecular Biology, DOI 10.1007/978, 1-4939-7142-8.

Kalinina et al., "Selective Detection of the D-enantiomer of 2-Hydroxyglutarate in the CSF of Glioma Patients with Mutated Isocitrate Dehydrogenase", Clin Cancer Res; 22(24) Dec. 15, 2016.

Kamerling et al., "Determination of the configurations of lactic and glyceric acids from human serum and utine by capillary gas-liquid chromatography", Journal of Chromatography, 143 (1977) 117–123.

Kamerling et al., "Determination of the absolute configuration of some biologically important Urinary 2-hydroxidicarboxylic acids by capillary gas-liquid chromatography", Journal of Chromatography, 222, 1981, 276-283.

Kranendijk et a., "Progress in understanding 2-hydroxyglutaric acidurias", J Inherit Metab Dis (2012) 35:571-587.

Lombardi et al., "Diagnostic Value of Plasma and Urinary 2-Hydroxyglutarate to Identify Patients With Isocitrate Dehydrogenase-Mutated Glioma", The Oncologist, 2015;20:562-567.

Losman et al., "What a difference a hydroxyl makes: mutant IDH, (R)-2-hydroxyglutarate, and cancer", Genes & Development 27:836-852, 2013.

Oldham et al., "Quantification of 2-Hydroxyglutarate Enantiomers by Liquid Chromatography-mass Spectrometry", Bio Protoc. Aug. 20, 2016; 6(16), HHS Public Access.

Patil et al., "Chiral Gas Chromatography", Chapter 11, Department of Chemistry and Biochemistry, University of Texas at Arlington, Arlington, TX, United States, 2018 Elsevier.

Rakheja et al., "Increased plasma D-2-hydroxyglutarate in isocitrate dehydrogenase 2-mutated blastic plasmacytoid dendritic cell neoplasm", Elsevier, Human Pathology, 2015, 46, 322-326.

Rashed et al., "Chiral liquid chromatography tandem mass spectrometry in the determination of the con®guration of 2-hydroxyglutaric acid in urine", Biomed. Chromatogr. 14: 317-320 (2000).

Rzem et al., "L-2-Hydroxyglutaric aciduria, a defect of metabolite repair", J Inherit Metab Dis (2007) 30:681-689.

Sahm et al., "Detection of 2-Hydroxyglutarate in Formalin-Fixed Paraffin-Embedded Glioma Specimens by Gas Chromatography/Mass Spectrometry", Brain Pathology 22 (2012) 26-31.

Seijo-Martínez et al., "L-2-Hydroxyglutaric Aciduria", Arch Neurol, vol. 62, Apr. 2005.

Senyilmaz et al., "Chicken or the egg: Warburg effect and mitochondrial dysfunction", F1000Prime Reports 2015, 7:41.

Sharma*, "Development of Novel Therapeutics Targeting Isocitrate Dehydrogenase Mutations in Cancer", Current Topics in Medicinal Chemistry, 2018, 18, 505-524.

Wood, "Metabolomics", Neuromethods 159, University of Saskatchewan, Saskatoon, SK, Canada, ISBN 978, 1, 0716-0863-0.

Struys et al., "Measurement of Urinary D- and L-2-Hydroxyglutarate Enantiomers by Stable-Isotope-Dilution Liquid Chromatography-Tandem Mass Spectrometry after Derivatization with Diacetyl-L-Tartaric Anhydride", Clinical Chemistry 50:8, 1391-1395 (2004).

Struys et al., "2-Hydroxyglutarate is not a metabolite; D-2-hydroxyglutarate and L-2-hydroxyglutarate are!", Letter, PNAS, Dec. 17, 2013, vol. 110, No. 51.

Tyrakis et al., "S-2-hydroxyglutarate regulates CD8+T-lymphocyte fate", 236, Nature, vol. 540, Dec. 8, 2016.

* cited by examiner

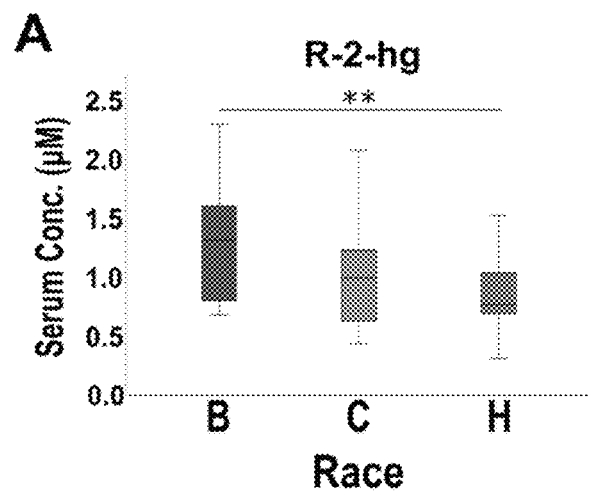 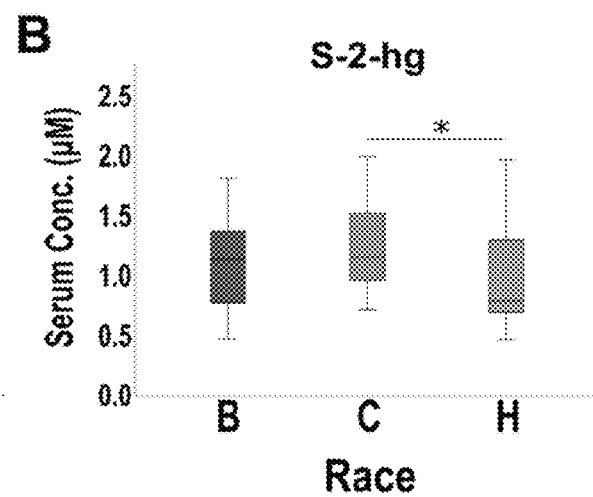
FIG. 2A  FIG. 2B
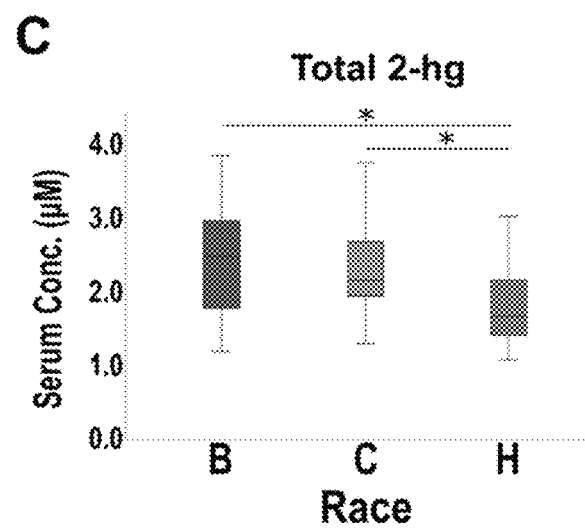 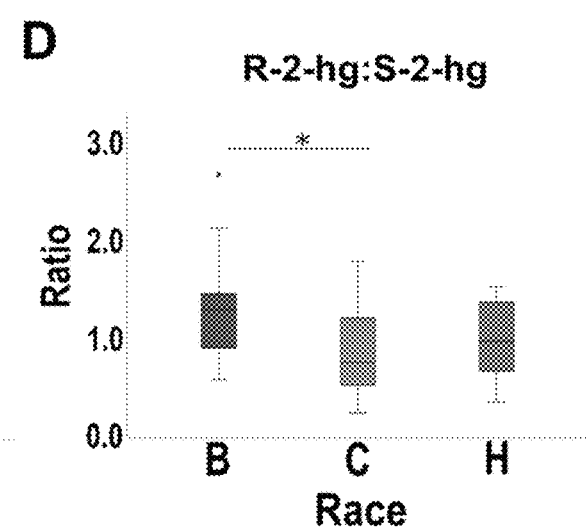
FIG. 2C  FIG. 2D
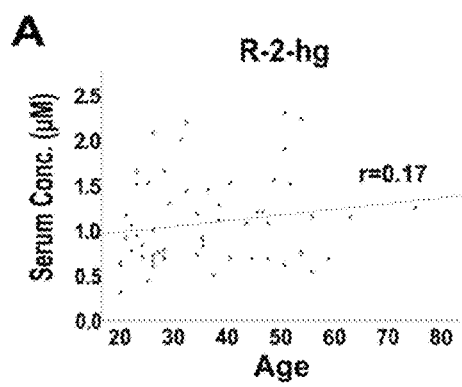 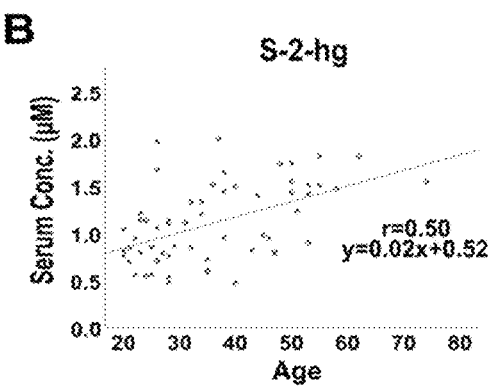
FIG. 3A  FIG. 3B

MEASUREMENT OF 2-HYDROXYGLUTARATE ENANTIOMER LEVELS AS A BIOMARKER FOR IDH MUTANT CANCERS

CROSS-REFERENCE TO RELATED APPLICATIONS

This application claims priority to U.S. Provisional Application Ser. No. 62/975,609, filed Feb. 12, 2020, the entire contents of which are incorporated herein by reference.

TECHNICAL FIELD OF THE INVENTION

The present invention relates in general to the field of biomarkers, and more particularly, to the measurement of 2-hydroxyglutarate enantiomer levels as a biomarker for isocitrate dehydrogenase (IDH) mutant cancers.

STATEMENT OF FEDERALLY FUNDED RESEARCH

None.

BACKGROUND OF THE INVENTION

Without limiting the scope of the invention, its background is described in connection with brain cancer.

(R)-2-hydroxyglutarate (R-2-hg) has gained significant interest as an oncometabolite and a circulating biomarker [1]. Cancers with isocitrate dehydrogenase (IDH) mutations, such as glioma and acute myeloid leukemia (AML), produce R-2-hg through a gain-of-function mutation of the enzyme [2,3]. R-2-hg is also normally produced in the body and is tightly regulated to keep intracellular levels low (<0.1 mM) [4]. Basal levels of R-2-hg are detectable in bodily fluids, making it accessible as a measurable biomarker. The development of accurate, reproducible assays to detect R-2-hg would therefore not only aid in the diagnosis of IDH mutation (IDHmut) related neoplasms but aid in the monitoring of treatment response and the detection of recurrence.

SUMMARY OF THE INVENTION

In one embodiment, the present invention includes a method of identifying 2-hydroxygluterate (2-hg) metabolites in a sample comprising: obtaining the sample from a patient; extracting the 2-hydroxygluterate (2-hg) metabolites from the sample without modifying a chiral center of the 2-hg metabolites; separating the one or more 2-hg metabolites in the sample using a chiral gas chromatography capillary column; and quantitating an amount of 2-hg metabolites in the sample using mass spectrometry (MS). In one aspect, the 2-hg metabolites are (R)-2-hydroxygluterate ((R)-2-hg) and (S)-2-hydroxygluterate ((S)-2-hg). In another aspect, the sample is a biological fluid. In another aspect, the biological fluid is chosen from at least one of: serum, urine cerebrospinal fluid, or sputum. In another aspect, the patient has, or is suspected of having, a tumor. In another aspect, the tumor has an isocitrate dehydrogenase (IDH) mutation. In another aspect, the the IDH mutation tumor is at least one of: an acute myeloid leukemia (AML), intrahepatic cholangiocarcinomas, central chondrosarcomas, breast cancer, or brain tumor. In another aspect, the tumor is a glioma tumor. In another aspect, the IDH mutation is an IDH1 or an IDH2 mutation. In another aspect, the IDH1 or IDH2 mutation causes an increase in an (R)-2-hg metabolite as compared to a reference level of (R)-2-hg metabolite from an individual without a tumor. In another aspect, an increase in a level of (R)-2-hg is indicative of an actively growing IDH mutant cancer. In another aspect, the method further comprises the step of treating the patient with an increase in the (R)-2-hg metabolite with at least one of: a chemotherapy, surgery, or radiation. In another aspect, the 2-hg metabolites are quantitated without at least one of: a second extraction step, a centrifugation step, or an incubation step. In another aspect, the mass spectrometry is selected from MS/MS, MS/MS fragmentation followed by Gas Chromatograph, or triple quadrupole MS.

In another embodiment, the present invention includes a method of tracking brain disease progression by quantitating an amount of (R)-2-hydroxygluterate ((R)-2-hg) in the sample using triple quadrupole mass spectrometry levels in a patient comprising: (a) obtaining a sample from the patient; (b) extracting 2-hg metabolites from the sample without modifying the chiral center of the 2-hg metabolites; (c) separating the 2-hg metabolites in the sample using a chiral gas chromatography capillary column; (d) quantitating an amount of the 2-hg metabolites in the sample using mass spectrometry; and (e) comparing the level of (R)-2-hg in the sample to an earlier patient sample; and if the (R)-2-hg levels are rising continue or increase treatment; or if the (R)-2-hg levels are stable or decreasing, decrease or cease treatment. In one aspect, the treatment includes at least one of chemotherapy, surgery, or radiation. In another aspect, the earlier sample was obtained 1, 2, 3, 4, 5, 6, 7, 8, 9, 10 days, weeks, or months prior to the sample obtained in step (a). In another aspect, the sample is a biological fluid. In another aspect, the biological fluid is selected from at least one of: a serum, urine cerebrospinal fluid, or sputum. In another aspect, the biological fluid is serum. In another aspect, the method further comprises detecting an IDH mutation in the patient selected from at least one of: an IDH1 or an IDH2 mutation. In another aspect, the IDH1 or IDH2 mutation causes an increase in an (R)-2-hg metabolite as compared to a reference level (R)-2-hg metabolite from an individual without a brain tumor. In another aspect, an increase in a level of (R)-2-hg is indicative of an actively growing IDH mutant cancer. In another aspect, the method further comprises obtaining one or more additional samples over a period of time to measure an increase or decrease in the (R)-2-hg levels, and continuing or discontinuing treatment depending on the increase or decrease in the (R)-2-hg levels. In another aspect, the mass spectrometry is selected from MS/MS, MS/MS fragmentation followed by Gas Chromatograph, or triple quadrupole MS.

In another embodiment, the present invention includes a single extraction method of identifying 2-hydroxygluterate (2-hg) metabolites in a sample comprising: (a) obtaining the sample from a patient; (b) extracting in a single step the 2-hydroxygluterate (2-hg) metabolites from the sample without modifying a chiral center of the 2-hg metabolites; (c) separating the one or more 2-hg metabolites in the sample using a chiral gas chromatography capillary column; and (d) quantitating an amount of 2-hg metabolites in the sample using mass spectrometry.

In another embodiment, the present invention includes a method for treating a patient with an IDH mutant tumor, the method comprising the steps of: determining whether the patient has an elevated (R)-2-hydroxygluterate ((R)-2-hg) level as compared to a subject without an IDH mutant tumor by: obtaining a serum sample from a patient; extracting 2-hg metabolites from the sample without modifying the chiral center of the 2-hg metabolites; separating the 2-hg metabolites in the sample using a chiral gas chromatography capillary column; and detecting the 2-hg metabolites in the sample using mass spectrometry; and quantitating an amount of 2-hg metabolites in the sample using mass spectrometry; and if the (R)-2-hg level of the patient is greater than an amount in a subject without an IDH mutation, then treating the patient with at least one of chemotherapy, surgery, or radiation.

BRIEF DESCRIPTION OF THE DRAWINGS

For a more complete understanding of the features and advantages of the present invention, reference is now made to the detailed description of the invention along with the accompanying figures and in which:

FIGS. 2A to 2D shows the serum levels of healthy donors by race. Differences in race of R-2-hg (FIG. 2A), S-2-hg (FIG. 2B), Total 2-hg (FIG. 2C), and 2-hg Ratio (FIG. 2D), vary according to the parameter B Black, C Caucasian, H Hispanic. **p-value<0.01, *p-value<0.05.

FIGS. 3A to 3D shows the correlation of R-2-hg (FIG. 3A), S-2-hg (FIG. 3B), Total 2-hg (FIG. 3C), and the 2-hg Ratio (FIG. 3D) vs. age. Pearson correlation statistic is shown for each graph and a linear fit equation is given if the Pearson correlation analysis was statistically significant.

DETAILED DESCRIPTION OF THE INVENTION

Figure 1A:
FIGS. 1A to 1C shows the separation and detection of 2-hg enantiomers using GC-MS/MS. Extracted serum sample is derivatized using TMS-DAM (A). Derivatized 2-hg is separated over a β-cyclodextrin column and two MRM transitions are monitored, 117>85 and 85>29 (B). Corresponding deuterium-labeled internal standards of 2-hg are also detected through the transitions, 120>88 and 88>32. Asterisks denote the position of deuterium atoms. A representative MRM of 2-hg chromatograms is shown demonstrating sufficient and sensitive separation of both enantiomers from healthy human serum (C).

While the making and using of various embodiments of the present invention are discussed in detail below, it should be appreciated that the present invention provides many applicable inventive concepts that can be embodied in a wide variety of specific contexts. The specific embodiments discussed herein are merely illustrative of specific ways to make and use the invention and do not delimit the scope of the invention.

To facilitate the understanding of this invention, a number of terms are defined below. Terms defined herein have meanings as commonly understood by a person of ordinary skill in the areas relevant to the present invention. Terms such as "a", "an" and "the" are not intended to refer to only a singular entity, but include the general class of which a specific example may be used for illustration. The terminology herein is used to describe specific embodiments of the invention, but their usage does not limit the invention, except as outlined in the claims.

(R)-2-hydroxyglutarate (R-2-hg) is a metabolite produced under physiologic conditions but also by tumors harboring isocitrate dehydrogenase (IDH) mutations. Detection of R-2-hg is challenging as it must be distinguished from its enantiomer (S)-2-hydroxyglutarate (S-2-hg), which is also produced in the body and its presence can increase under hypoxic conditions. A chiral gas chromatography-tandem mass spectrometry (GC-MS/MS) assay was developed which separated enantiomers using a chiral column and quantified levels using a stable-isotope internal standard. The assay taught herein improves upon current methods by avoiding chiral derivatization and uses a simplified sample extraction procedure. The assay was validated and serum 2-hg levels from healthy patients were measured, establishing a new, comprehensive reference range for normal levels of each enantiomer. Differences in basal levels were observed between races but not sex. Age also correlated with S-2-hg levels but not R-2-hg levels. Finally, serum levels of 2-hg enantiomers were measured in a pilot study of 11 patients with and without IDH mutant gliomas. An increase in R-2-hg levels was observed in 2/3 patients with actively growing IDH mutant gliomas. S-2-hg levels were increased in 4/11 patients, irrespective of IDH status. The results presented demonstrate the use of a GC-MS/MS assay for measurement of 2-hg enantiomer levels for clinical use.

The critical need for an 2-hg enantiomer assay has heightened with the recent development of therapies targeting the IDH mutant enzyme [5]. However, the measurement of circulating R-2-hg levels can be confounded by the enantiomer (S)-2-hydroxyglutarate (S-2-hg), which is produced by the body under physiologic conditions [6,7]. S-2-hg is regulated by different enzymes than R-2-hg, such as that each enantiomer has levels independent of the other. For instance, levels of S-2-hg are not altered by IDH mutations [2] but are influenced by T-cell receptor activation [8], complex I inhibition [9], S-2-hg dehydrogenase (S-2HGDH) deficiencies [10], and most notably, hypoxia [11], which has major implications in tumor biology. Therefore, it is important to accurately and precisely distinguish between the two enantiomers to detect and utilize R-2-hg as a biomarker of disease for patients with IDHmut tumors.

Methods used to separate and detect 2-hg enantiomers were initially developed to detect levels in the urine of patients with inborn errors of metabolism by means of chiral derivatization [12-14]. Diastereomers of 2-hg were created by derivatization with (R)-(−)-2-butanol, separated over an achiral gas chromatography (GC) column, and detected by mass spectrometry (MS). The method results in significant racemization (5-7%) and is not suitable for applications that require accurate and sensitive methodologies, such as the detection of changes in serum 2-hg enantiomer levels from a brain tumor with a complex blood-brain tumor barrier [15]. Other chiral derivatization agents, such as Diacetyl-L-tartaric anhydride (DATAN) [16] and N-(o-toluenesulfonyl)-L-phenylalanyl chloride (TSPC) [17] has gained traction for use in Liquid Chromatography-tandem Mass Spectrometry (LC-MS/MS). Though DATAN results in less racemization, it is not completely absent, and it requires evaporation of all water pre-derivatization, the use of heat during derivatization, and re-suspension in a new solution post-derivatization. Furthermore, derivatization with TSPC requires the use of hazardous pyridine, significantly lengthens the retention times from 4-8 minutes to 21-23 minutes, and the racemization data was not reported.

Utilization of a chiral column, which avoids the use of any chiral derivatization and its associated drawbacks, is an alternative method to separate 2-hg enantiomers. Chiral columns contain a chiral stationary phase (CSP), which has a higher affinity for one enantiomer over the other. LC chiral columns are commercially available but are costly and some have not been validated for use with MS to measure 2-hg enantiomers [18-20]. Chiral separation using GC columns is a mature method and as a result, a variety of robust CSPs exists [21]. Since commercial chiral columns have become widely available across multiple vendors, the price of chiral GC columns is comparable to standard achiral reverse phase LC columns. Therefore, chiral GC columns are now amenable for use in a variety of applications, including clinical assays [21].

A proper assay to detect 2-hg enantiomers also requires a range of normal values to distinguish between physiological levels vs. pathological levels. Currently, a solid reference range for normal levels of each 2-hg enantiomer is lacking. Previous studies reporting normal values of serum 2-hg levels either only measured total 2-hg levels [22,23], reported the ratio of 2-hg enantiomers [24], or only reported 2-hg enantiomer levels relative to IDHwt levels [24-26]. Other studies that did include a range of normal values did not specify from where the reported references values arose [27-30]. Furthermore, the studies in the human metabolome database that report adult 2-hg enantiomer levels cite pediatric studies [31-33]. Therefore, definitive cutoffs for normal limits have not been established, and it is unknown if reference values for children are different from adults [34].

The present invention has two demonstrable outcomes. First, is the development and validation of a novel GC-MS/MS assay that encompasses the use of a chiral GC capillary column to separate 2-hg enantiomers with subsequent sensitive, specific detection by triple quadrupole (QqQ) MS. Thus, it was possible to create an inexpensive, simple assay for clinical use. It was also possible to develop a modified ethyl acetate-based extraction of 2-hg from serum where the metabolites were volatilized without racemization. Previous studies that utilized chiral GC columns were performed using urine samples where 2-hg levels were physiologically higher as compared to serum. Furthermore, these assays were limited by poor specificity as they utilized low resolution, single-quad GC-MS instruments.

The second outcome was to expand the range and reference values for normal physiological levels of 2-hg enantiomers and to demonstrate the feasibility of the assay for patients with IDHmut gliomas. The results herein address these issues and to provide an expected range of values for each 2-hg enantiomer within sera of healthy individuals 18 years and older. Levels were stratified according to race, sex, and age to elucidate basal levels and normal ranges of 2-hg enantiomers. Lastly, the applicability of this assay for clinical use is demonstrated by measuring 2-hg enantiomers in the blood of patients with and without IDHmut gliomas.

Materials and Methods. Chemicals and Reagents. D-α-Hydroxyglutaric acid disodium salt (≥98%), and L-α-Hydroxyglutaric acid disodium salt (≥98%) standards were purchased from Millipore Sigma (St. Louis, Mo.). The deuterated internal standard (IS), Disodium (RS)-2-Hydroxy-1,5-pentanedioate-2,3,3-d3, OD (≥95%), was purchased from CDN Isotopes (Pointe-Claire, Quebec). GC-MS grade ethyl acetate, hydrochloric acid solution (6.0N), sodium chloride (NaCl, ≥99%), glacial acetic acid (≥99%), and (Trimethylsilyl)diazomethane ((TMS)DAM) solution (2.0M) in Hexanes, were purchased from Millipore Sigma (St. Louis, Mo.). LC-MS grade methanol and LC-MS grade $H_2O$ were obtained from J.T. Baker (Phillipsburg, N.J.).

Human Serum Samples. Serum from 60 individual healthy donors was obtained from Innovative Research (Novi, Mich., USA). Samples were equally divided among Caucasian, Black and Hispanic races and across each sex (Table 1). After thawing, each serum sample was aliquoted and stored at −80° C. Freeze-thaw cycles of any sample used in this study were kept at a maximum of two. Eleven sera samples from patients with IDH mutated or IDH wild-type (IDHwt) gliomas were collected from an ongoing, IRB-approved study at The Austin Brain Tumor Center (Texas Oncology, Austin, Tex.).

TABLE 1

Demographics of healthy human donors used for measurement of serum 2-hg enantiomers.

| Demographic | | N | Age Mean +/− SD (yrs.) | Age Range (yrs.) |
|---|---|---|---|---|
| All | | 60 | 35.97 +/− 12.62 | 20-74 |
| Race | Black (B) | 20 | 36.75 +/− 12.19 | 21-62 |
| | Caucasian (C) | 20 | 38.10 +/− 14.08 | 20-74 |
| | Hispanic (H) | 20 | 33.05 +/− 11.55 | 20-58 |
| Sex | Female (F) | 30 | 37.63 +/− 13.82 | 20-74 |
| | Male (M) | 30 | 34.30 +/− 11.28 | 20-58 |

Assay Validation. All standards were prepared by dissolving 1 mg of powder into the appropriate amount of $H_2O$ to make two different 1 mM stock solutions, one stock for determination of linearity and limits of detection and the other for quality controls (QCs). All stock solutions were aliquoted and stored at −80° C.

Linearity and Limits of Detection. Serial 1:10 dilutions of 1 mM and 0.5 mM to 0.1 and 0.5 respectively, were used to test linearity. Ten microliters of each sample were used for analysis and prepared for GC-MS/MS analysis as described below. Each data point was normalized to 10 μL of a 10 μM solution of deuterated 2-hg. Limits of detection were reported using two different metrics. The instrument detection limit (IDL) and Lower Limit of Quantitation (LLoQ) were determined by injecting 8 technical replicates of the 1 μM solution, from three separate dilutions on three separate days. IDL is determined by the following equation t*RSD*concentration/100, where t is the 99% confidence level for n−1 degrees of freedom and RSD is the relative standard deviation. The second metric, LLOQ was defined as the amount injected onto the column with an RSD≤20%.

Quality Controls, Accuracy, Precision. Ten microliters of four different QCs at 3 μM (Low QC), 8 μM (Mid-Low QC), 40 μM (Mid QC), 90 μM (High QC), plus LLoQ, were used to assess the accuracy and precision of the assay. Accuracy and precision were assessed over three separate dilutions where each dilution had three technical replicates run for three aliquots of each QC. Each new dilution was run on one day and used to analyze intra-assay variability between the three aliquots and technical replicates of each aliquot. Inter-assay variability compared accuracy and precision across all three separate dilutions. Inter-assay precision of the extraction method was measured by calculating the RSD of three biological replicates of each serum sample as measured on three different days.

Selectivity and Specificity, Recovery, Carry-over, and Stability. Selectivity and specificity were demonstrated by measuring 2-hg enantiomers signals from the extraction of 5 blank samples (i.e., no added serum), 5 PBS samples, and 5 vials with only derivatization reagents. Recovery was assessed by comparing serum samples spiked with deuterated 2-hg before and after extraction where 10 μL of three concentrations, 3 μM, 30 μM and 90 μM in a total of 15 different serum samples were used (five each). Carryover was assessed by measuring 2-hg enantiomer levels after injecting a blank solvent, such as ethyl acetate or acetonitrile, between experiments analyzing QC and serum samples. Lastly, stability was assessed by comparing the change in concentration (by percent difference) after 24 hours in the autosampler, 4 hours on the bench top, and 4 freeze-thaw cycles (5 separate serum samples per experiment).

Sample Preparation. Serum Extraction. Two-hundred fifty microliters of serum were added to a 1.5 mL microcentrifuge tube, followed by 3 µL of deuterated 2-hg (100 µM) IS, and 10 µL of 6 N HCl. Sodium chloride was then added to saturation and the tube was vortexed for 30 s. One milliliter of ethyl acetate was subsequently added to the tube, followed by a second 30 s vortex. The sample was then centrifuged for 5 min at 4000×g. Nine hundred microliters of the top organic layer were then pipetted into a 2 mL glass vial and dried by vacuum centrifugation.

Derivatization. Derivatization was performed to volatilize the metabolites and not for the purposes of separation. To a dried sample in a glass tube was added 100 µL of methanol and 20 µL of 2.0 M (TMS)DAM in hexanes. The sample was then capped for derivatization and placed on a mixer at room temperature (25° C.) for 30 min. Upon completion of derivatization, 20 µL of acetic acid was added to quench the reaction, and the vial was capped for GC-MS/MS analysis.

Separation and Detection of 2-hg Enantiomers. Sera levels of 2-hg enantiomers were separated and measured using a Gas-Chromatography Triple Quadrupole (GC-QQQ) Mass Spectrometer (Shimadzu, Kyoto, Japan) equipped with a CP-Chirasil-Dex CB column, 0.25 mm×25 m×25 µm (Agilent, Santa Clara, Calif.). One microliter of the derivatized sample was injected into the GC splitless inlet set at 220° C. with an initial oven temperature of 80° C. The GC was programmed to sample for one minute at 80° C., after which the oven was ramped at 4° C./min to 180° C. and held for 4 minutes for a total run time of 30 min. The column flow was set at 1.5 mL/min using constant linear velocity with helium as the carrier gas.

The MS parameters were set as follows: interface temperature 200° C., ion source temperature 200° C., solvent cut time 4 min, and an event time of 0.04 sec. The ion source ionization energy was set at 70 eV to produce positive ions. The following transitions were monitored, 85.00 m/z>29.00 m/z and 88.00 m/z>32.00 m/z at 13.00 V collision energy, and 117.00 m/z>85.00 m/z and 120.00 m/z>88.00 m/z at a collision energy of 6.00 V. 2-hg enantiomer peaks were integrated using the Shimadzu Postrun Analysis Software and quantitation of endogenous 2-hg enantiomer levels was measured relative to the IS. Total 2-hg is defined as the sum of each absolute 2-hg level and the 2-hg Ratio as R-2-hg:S-2-hg. Reported serum levels were averages of three technical replicates.

Statistics. The distributions of R-2-hg, S-2-hg, Total 2-hg, and the 2-hg Ratio were not normally distributed when split by race or sex, nor were the variances equal between each race and sex. Thus, an aligned rank transform was used to perform a nonparametric, two-way ANOVA to compare differences in R-2-hg, S-2-hg, Total 2-hg, 2-hg Ratio, across race and sex [35]. The residuals were normally distributed, homoscedastic, and had only one outlier for all parameters as a function of age. Therefore, a linear regression and Pearson correlation was used to characterize any correlation between age and any 2-hg parameter. Pearson correlation significance was assessed using an ANOVA test.

GC-MS/MS Assay for Separation and Detection of 2-hg Enantiomers from Serum. To measure levels of 2-hg enantiomers in serum, a novel chiral GC-MS/MS assay was developed. To volatilize 2-hg, the carboxylic acid functional groups were converted into methyl esters using (TMS)DAM (FIG. 1A). Derivatization with (TMS)DAM is advantageous as it requires no heat and only small quantities of reagent are needed. The chiral center is not modified during (TMS)DAM derivatization, avoiding the racemization that occurs with chiral derivatization reagents such as DATAN and (R)-(−)-2-butanol (Supplemental FIG. 1). The derivatization time implemented in this study was 30 minutes at room temperature (25° C.).

Figure 1B:
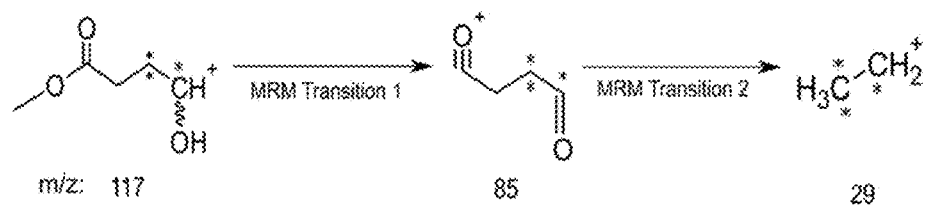

Targeted detection and quantitation of 2-hg enantiomers were performed using multiple reaction monitoring (MRM) where two primary transitions were monitored. FIG. 1B shows the molecular structures of the ion species for each MRM transition. MRM transition 1 captures the loss of the second methyl ester functional group, and MRM transition 2 detects the loss of two carbon-oxygen bonds from either end. The tri-deuterated internal standard undergoes an identical fragmentation as the endogenous compound. Positions of the three deuterium atoms are denoted by asterisks in FIG. 1B.

Figure 1C:
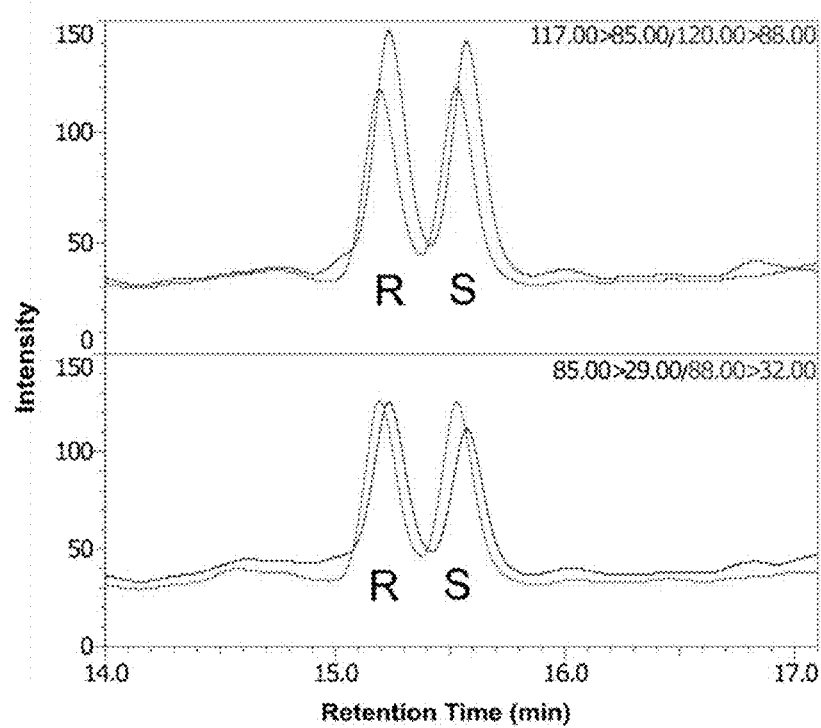

Typical MRM chromatograms of 2-hg enantiomers as measured in serum is represented in FIG. 1C. Next, 2-hg enantiomers were separated using a commercially available β-cyclodextrin chiral column with a retention time of approximately 15.20 min and 15.55 min for R-2-hg and S-2-hg, respectively. Retention times were comparable to previously reported retention times using a commercially-available β-cyclodextrin column, but with improved resolution of the enantiomers [36]. Despite shorter retention times reported for DATAN LC methods (4-8 min.), the overall run time for the LC method is 30 minutes due to the equilibration time. The GC-MS/MS method reported here also has an overall runtime of 30 minutes. The 30-minute runtime for the GC-MS/MS method allows for the elution of any retained analytes and for the robust separation of 2-hg enantiomers from sample-to-sample without the loss of resolution, intensity, or sample carryover.

Simplified Metabolite Extraction Protocol. The ethyl acetate extraction protocol was modified from previous methods that were utilized for the extraction of organic acids from urine [37-39]. The method employed herein was optimized for clinical use by reducing the organic solvent volume as well as eliminating an incubation step and a second solvent-solvent extraction step. Prior studies using an ethyl acetate based-extraction method utilized ethyl acetate (EA) volumes up to 5 mL [37,39]. In the current study, this volume has been reduced to 1 mL, allowing the extraction to be carried out in one glass vial, while also keeping a sufficient sample to organic solvent volume ratio (1:4).

The assay was further optimized by eliminating an incubation step between the collection of the extraction layer and the subsequent centrifugation step, eliminating a drying step with sodium sulfate, and removing a second 5 mL EA re-extraction step. Repeated solvent-solvent extraction with a second 5 mL of ethyl acetate did improve yield (data not shown), but the signal-to-noise, accuracy, and precision (as discussed in the Method Validation section) from only one ethyl acetate extraction step were sufficient. Additionally, the method taught herein is also advantageous over extractions using 80% MeOH at low temperatures (−80° C.) by drastically reducing incubation periods. Methods using 80% MeOH can require incubation times of 6-8 hrs, and access to dry ice temperatures. The present invention eliminates the need for the incubation step and/or use of dry ice, neither of which are necessary for the practice of the present invention. Overall, the method of the present invention significantly improved sample preparation by reducing the number of steps and the total extraction time.

FIGS. 1A to 1C shows the separation and detection of 2-hg enantiomers using GC-MS/MS. Extracted serum sample is derivatized using TMS-DAM (FIG. 1A). Derivatized 2-hg is separated over a β-cyclodextrin column and two MRM transitions are monitored, 117>85 and 85>29 (FIG. 1B). Corresponding deuterium-labeled internal standards of 2-hg are also detected through the transitions, 120>88 and 88>32. Asterisks denote the position of deuterium atoms. A representative MRM of 2-hg chromatograms is shown demonstrating sufficient and sensitive separation of both enantiomers from healthy human serum (FIG. 1C).

Assay Validation. The results of the method validation are summarized in Table 2. A linear instrument response was observed from 35.7 fmol to 14.3 pmol injected on to the column. The assay demonstrated a high sensitivity with an IDL of 16.3 fmol for R-2-hg, 19.7 fmol for S-2-hg and an LLOQ of 71.4 fmol for both enantiomers. This is an improved sensitivity over DATAN-based LC-MS/MS methods and comparable to the method using TSPC derivatization. According to the Federal Drug Administration (FDA) guidelines for Bioanalytical Method Validation, the target accuracy for each QC sample must be within 15% with a ≤15% CV (precision) and within 20% and 20% CV at the LLoQ level [40]. All measurements of precision and accuracy for the assay fell well within the recommended target values. Intra-assay values of accuracy and precision for each of the three days are shown as a range. The average inter-assay variability for all serum samples was observed to be 9.8% for R-2-hg, and 10.0% for S-2-hg ranging.

Each injection of a blank extraction, PBS, or derivatization solution resulted in no measurable signal above background for either 2-hg enantiomer. Although, the ideal test of selectivity, specificity, and matrix effects involve a sample with and without the metabolites of interest, so far, no serum sample exists that is absent of 2-hg enantiomers. As expected by utilizing a simplified extraction protocol, the recovery was not 100% and ranged from 15.6-23.0% for R-2-hg and 11.1-21.2% for S-2-hg. However, the signal-to-noise as demonstrated in FIGS. 1A to 1C, and the sensitivity and precision as shown in Table 2, is sufficient to counter-balance what is lost in the recovery. Additionally, FDA guidelines do not necessitate 100% recovery, only consistency and reproducible results, the present invention demonstrates the serum precision data necessary to FDA requirements. Lastly, the serum samples were shown to be stable in the autosampler after 24 hours (1.6±1.3 & 1.2±0.7%-difference) and at room temperature for up to 4 hours (6.4±5.0 & 5.3±5.2%-difference) for each enantiomer. However, four freeze-thaw cycles consistently and drastically reduced the amount of 2-hg measured by 35.8 to 40.4%.

Basal Levels of 2-hg Enantiomers from Normal Sera. Levels of 2-hg enantiomers were measured in serum from 60 healthy human donors (Table 3). The average levels and the 95% confidence interval of serum R-2-hg and S-2-hg were comparable at 1.09 (0.97-1.21) μM and 1.11 (1.00-1.22) μM, respectively. Accordingly, the average ratio of serum 2-hg levels, R-2-hg:S-2-hg, was observed to be approximately 1:1 at 1.07 (0.95-1.20). The average Total 2-hg level, defined as R-2-hg+S-2-hg, was 2.20 (2.01-2.39) μM. Levels of each individual 2-hg enantiomer, along with the quartiles, are in accord with previous studies that reported values of 0.12-1.78 μM for R-2-hg and 0.04-1.5 μM for S-2-hg [27-29,41]. Total 2-hg levels were also in accord with previously reported values of 0.7-3.6 μM [22, 24, 33, 42-46]. Of note, the maximum individual values of R-2-hg and S-2-hg, 2.30 and 2.00 are higher than the previously reported normal values. Several reasons could exist for the discrepancy. The acquired serum samples are tested for commonly found infectious diseases but are not screened for IDHmut malignancy or other metabolic disorders.

Levels of R-2-hg and S-2-hg were also equally stratified by race (N=20 per group) and sex (N=30 per group). Basal levels of R-2-hg measured in Black (B) donors was 1.34 (1.10-1.58) which was a significant increase over the levels measured in Hispanic (H) donors at 0.87 (0.74-1.00) μM (p=0.004) (FIG. 2A.) Serum levels of R-2-hg for Caucasians (C) was measured at 1.06 (0.83-1.29) μM and was not significantly different from Black (p=0.362) and hispanic (p=0.114) sera. R-2-hg is regulated by the mitochondrial enzymes, hydroxyacid-oxoacid transhydrogenase (HOT) and R-2-hg dehydrogenase (R-2HGDH), and although there are no reported differences in activities of HOT or R-2HGDH according to race or ethnicity, it has been shown that some metabolic enzymes can have variable activity due to the expression of different isoenzymes [47].

TABLE 2

GC-MS/MS Validation.

|  | R-2-hg | S-2-hg |
| --- | --- | --- |
| Linear Dynamic Range (fmol-pmol) | 35.7-14.3 | 35.7-14.3 |
| Limits of Detection (fmol) | | |
| IDL | 16.3 | 19.7 |
| LLoQ | 71.4 | 71.4 |
| Accuracy (% Error) | | |
| Intra-assay | | |
| High QC | 2.2-3.2 | 2.4-3.4 |
| Mid QC | 1.1-7.0 | 3.0-3.5 |
| Mid-Low QC | 4.2-5.9 | 3.8-5.7 |
| Low QC | 6.2-9.1 | 3.1-8.3 |
| LLOQ | 9.0-13.2 | 8.7-11.1 |
| Inter-assay | | |
| High QC | 2.7 | 3.0 |
| Mid QC | 4.3 | 3.2 |
| Mid-Low QC | 5.0 | 4.9 |
| Low QC | 7.3 | 5.2 |
| LLOQ | 10.9 | 9.8 |
| Precision (CV %) | | |
| Intra-assay | | |
| High QC | 1.9-2.6 | 1.6-4.0 |
| Mid QC | 1.3-3.6 | 2.7-4.2 |
| Mid-Low QC | 2.8-4.1 | 0.7-2.9 |
| Low QC | 4.7-5.8 | 1.6-4.1 |
| LLOQ | 7.7-9.6 | 7.3-11.1 |
| Inter-assay | | |
| High QC | 2.3 | 3.0 |
| Mid QC | 2.6 | 3.3 |
| Mid-Low QC | 3.4 | 2.0 |
| Low QC | 5.2 | 3.2 |
| LLOQ | 8.8 | 9.7 |
| Serum | 9.8 | 10.0 |
| Selectivity/Specificity | | |
| PBS/Blank Extraction/ Derivatization Solution | No signal | No signal |
| Recovery (%) | | |
| High QC | 15.6 ± 6.9 | 11.1 ± 6.8 |
| Mid QC | 18.9 ± 3.8 | 17.1 ± 4.6 |
| Low QC | 23.0 ± 1.9 | 21.2 ± 1.2 |
| Stability (% Difference) | | |

TABLE 2-continued

GC-MS/MS Validation.

|  | R-2-hg | S-2-hg |
|---|---|---|
| 24-hour autosampler | 1.6 ± 1.3 | 1.2 ± 0.7 |
| 4-hour at Room Temp. | 6.4 ± 5.0 | 5.3 ± 5.2 |
| Freeze-Thaw ×4 | 35.8 ± 5.7 | 40.4 ± 9.3 |

TABLE 3

Levels of R-2-hg, S-2-hg, Total 2-hg, and 2-hg Ratio in serum of healthy donors. All values shown are reported in µM.

|  | Race | Mean (95% CI) | Min-Max | Q1 | Q2 | Q3 | 95th percentile | Proposed Cutoffs (Mean + 3*SD) |
|---|---|---|---|---|---|---|---|---|
| R-2-hg | All | 1.09 (0.97-1.21) | 0.32-2.30 | 0.71 | 0.98 | 1.41 | 2.19 | 2.52 |
|  | B | 1.34 (1.10-1.58) | 0.69-2.30 | 0.79 | 1.32 | 1.63 | 2.30 | 2.89 |
|  | C | 1.06 (0.83-1.29) | 0.44-2.08 | 0.63 | 1.00 | 1.24 | 2.08 | 2.55 |
|  | H | 0.87 (0.74-1.00) | 0.32-1.53 | 0.69 | 0.77 | 1.06 | 1.52 | 1.71 |
| S-2-hg | All | 1.11 (1.00-1.22) | 0.48-2.00 | 0.79 | 1.05 | 1.47 | 1.82 | 2.35 |
|  | B | 1.09 (0.90-1.28) | 0.48-1.82 | 0.77 | 1.15 | 1.40 | 1.82 | 2.31 |
|  | C | 1.27 (1.10-1.44) | 0.73-2.00 | 0.96 | 1.16 | 1.54 | 1.99 | 2.37 |
|  | H | 0.97 (0.77-1.17) | 0.48-1.98 | 0.70 | 0.80 | 1.39 | 1.96 | 2.24 |
| Total 2-hg | All | 2.20 (2.01-2.39) | 1.08-3.86 | 1.63 | 2.09 | 2.75 | 3.65 | 4.36 |
|  | B | 2.43 (1.20-2.81) | 1.20-3.86 | 1.73 | 2.49 | 2.97 | 3.85 | 4.86 |
|  | C | 2.33 (2.03-2.64) | 1.30-3.76 | 1.92 | 2.16 | 2.74 | 3.76 | 4.29 |
|  | H | 1.84 (1.57-2.10) | 1.08-3.03 | 1.40 | 1.67 | 2.17 | 3.02 | 3.53 |
| 2-hg Ratio | All | 1.07 (0.95-1.20) | 0.26-2.70 | 0.66 | 1.06 | 1.39 | 1.80 | 2.50 |
|  | B | 1.31 (1.08-1.54) | 0.61-2.70 | 0.92 | 1.32 | 1.49 | 2.67 | 2.80 |
|  | C | 0.89 (0.68-1.09) | 0.26-1.81 | 0.53 | 0.78 | 1.24 | 1.80 | 2.18 |
|  | H | 1.02 (0.83-1.21) | 0.37-1.56 | 0.66 | 0.99 | 1.41 | 1.55 | 2.24 |

The differences detected for S-2-hg serum levels across races were different from those for R-2-hg (FIG. 2B). S-2-hg levels for Caucasian sera were 1.27 (1.10-1.44) which was higher than levels measured in Hispanic sera at 0.97 (0.77-1.17) µM (p=0.019). Black S-2-hg levels were 1.09 (0.90-1.28) µM which were not significantly different compared to Hispanic levels (p=0.402) or Caucasian levels (p=0.301). Similar to R-2-hg, there are no reported differences in S-2-hg regulatory enzymes according to race or ethnicity. More information regarding the biology of serum R- and S-2-hg is needed to better interpret the observed differences in race, especially since the differences in race of basal R-2-hg levels were different than S-2-hg.

Total 2-hg levels for Hispanics at 1.84 (1.57-2.10) µM were lower as compared to Black serum levels at 2.43 (1.20-1.81) µM (p=0.170) and Caucasians levels at 2.33 (2.03-2.64) µM (p=0.030) (FIG. 2C). No differences were observed between Black and Caucasian total 2-hg levels (p=0.974). The ratio of the two enantiomers, R-2-hg:S-2-hg, were different between the average Black ratios at 1.31 (1.08-1.54) and Caucasian ratios at 0.89 (0.68-1.09) (p=0.024), but no differences were found in the ratios between Black vs. Hispanic (p=0.189) and Caucasian vs. Hispanic (p=0.620), where Hispanic ratios levels were 1.02 (0.83-1.21) (FIG. 2D). Black donors had one outlier with a ratio of 2.70, above the max boxplot whisker. Though the value does not represent the majority of the Black donor ratios, it is important to note that the individual R-2-hg value, 1.53 µM, and S-2-hg value, 0.57 µM, were normal demonstrating that the 2-hg ratio alone is likely not a sufficient marker of disease. Finally, no significant differences were observed between sexes (Male vs. Female) for all parameters, which is in agreement with previous studies (FIG. 5).

FIGS. 2A to 2D shows the serum levels of healthy donors by race. Differences in race of R-2-hg (A), S-2-hg (B), Total 2-hg (C), and 2-hg Ratio (D), vary according to the parameter. B Black, C Caucasian H Hispanic. **p-value<0.01, *p-value<0.05.

Proposed upper limit cutoffs for this assay, which were calculated as three standard deviations above the mean, would be 2.52 µM for R-2-hg, 2.35 µM for S-2-hg, 4.86 µM for total 2-hg, and 2.50 for the ratio. The results of this study also suggest that different cutoffs may need to be considered when determining an absolute increase in 2-hg enantiomer levels for different races. For example, high R-2-hg levels for a Hispanic patient could be deemed normal in a person of the Black race. The use of percent differences in temporal studies could also be used to aid in interpretation and bypass some of the differences observed in basal levels according to race. However, a larger sample size with a wider variety of races is needed to validate the reported findings, especially as the determination of proper cut-off values for IDHmut status is continually evaluated [24,26,34].

Figure 3C:
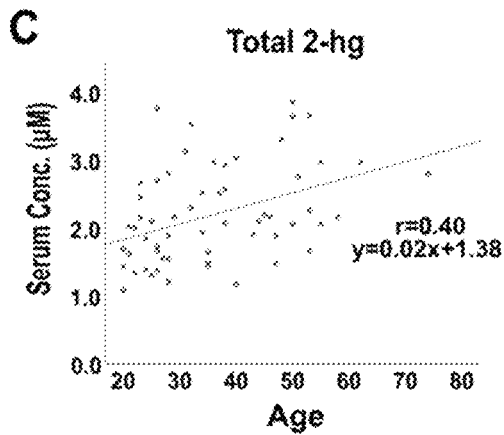
Figure 3D:
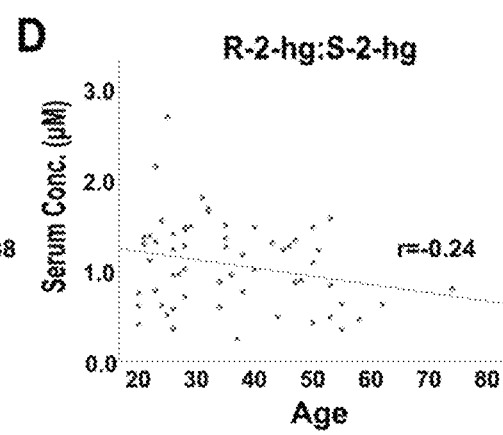

Correlation of 2-hg Enantiomer Levels with Age. The study population was young on average, 35.97+/−12.62 (SD) yrs. of age, with a range between 25 and 74. A Pearson correlation was used to determine if any correlation existed between age and R-2-hg, S-2-hg, Total 2-hg or the 2-hg Ratio. FIG. 3A-B demonstrates that R-2-hg did not shown any significant correlation, to age (p=0.191, r=0.17), while S-2-hg showed a significant, moderate correlation with age (p=0.000, r=0.50). Total 2-hg levels also demonstrated significant, moderate correlation with age (p=0.001, r=0.40), but the ratio of 2-hg enantiomers did not (p=0.061, r=−0.24) (FIG. 3C-D).

There is evidence that age is associated with an increase in minimal but chronic, systemic inflammation in the absence of active infection [48]. This age-related inflammation is largely attributed to mitochondrial dysfunction and DNA damage response pathway alterations, among others. Regulation of 2-hg includes mitochondrial enzymes and the effects of mitochondrial dysfunction on 2-hydroxyglutarate have been discussed elsewhere [49,50]. Any link between S-2-hg, age, and inflammation needs further investigation but is warranted from the correlations presented herein. Though incorporation of older patients into this study would help elucidate any correlation between age and S-2-hg, the focus was on a younger population as IDH mutant gliomas are associated with a younger age at presentation and secondary glioblastomas, which arise from lower-grade IDHmut gliomas, and which are predominately found in younger patients (median age of 45 yrs.) [51].

Figure 4:
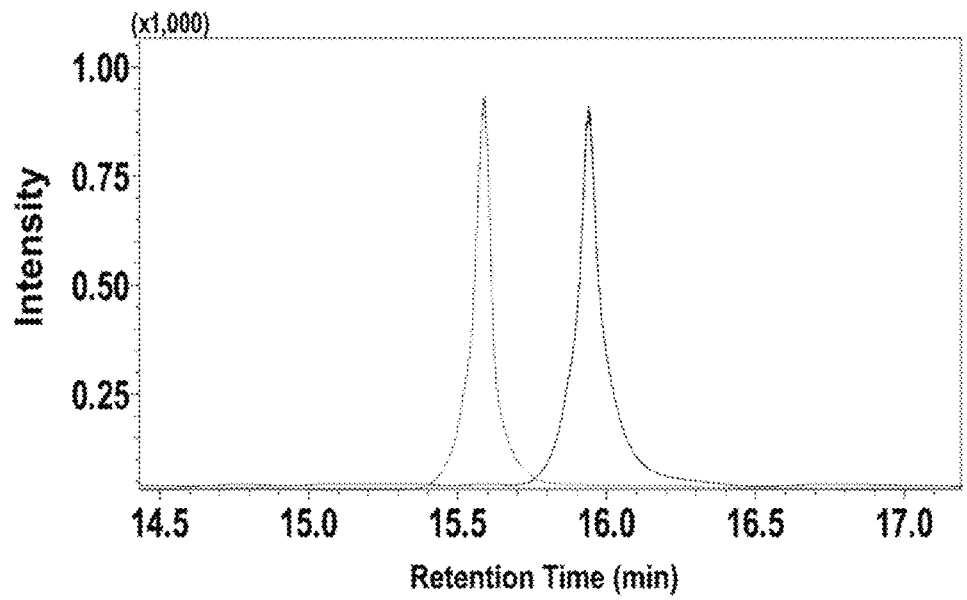
FIG. 4 shows a superimposed chromatogram of separate runs of derivatized R-2-hg (magenta) and S-2-hg (black) standards demonstrating the absence of racemization.
Figure 5A:
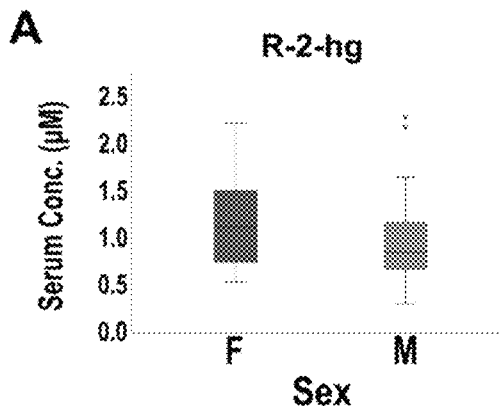
FIGS. 5A to 5D shows the serum levels of healthy donors by sex. No differences were observed between sex for R-2-hg (FIG. 5A), S-2-hg (FIG. 5B), Total 2-hg (FIG. 5C), and 2-hg Ratio (FIG. 5D).
Figure 5B:
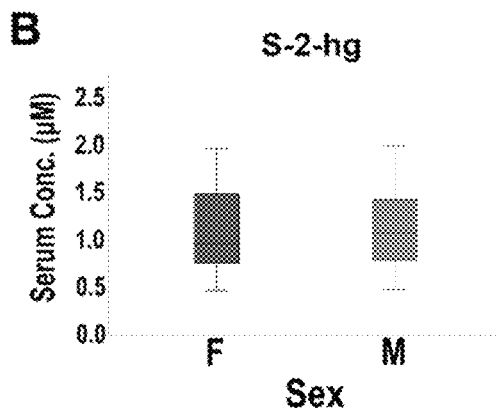
Figure 5C:
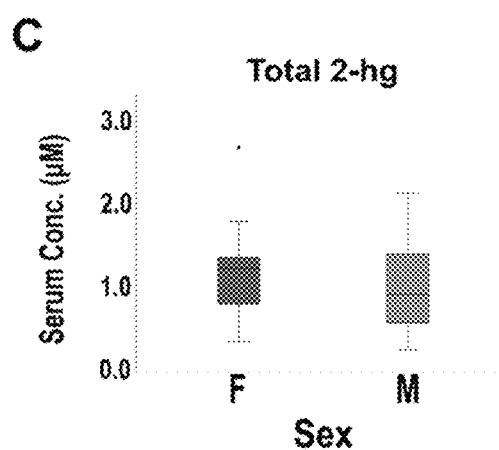
Figure 5D:
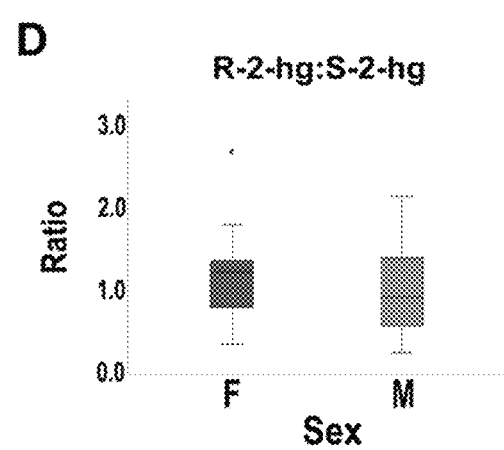

FIGS. 3A to 3D show the correlation of R-2-hg (FIG. 3A), S-2-hg (FIG. 3B), Total 2-hg (FIG. 3C), and the 2-hg Ratio (FIG. 3D) vs. age. Pearson correlation statistic is shown for each graph and a linear fit equation is given if the Pearson correlation analysis was statistically significant. FIG. 4 shows a superimposed chromatogram of separate runs of derivatized R-2-hg (magenta) and S-2-hg (black) standards demonstrating the absence of racemization. FIGS. 5A to 5D shows the serum levels of healthy donors by sex. No differences were observed between sex for R-2-hg (FIG. 5A), S-2-hg (FIG. 5B), Total 2-hg (FIG. 5C), and 2-hg Ratio (FIG. 5D).

Measurement of 2-hg Enantiomer Levels in Patients with IDH Mutant Gliomas. To demonstrate clinical feasibility for this assay to be used in patients with gliomas, a serum analysis in a pilot study of 11 patients with IDHmut and IDHwt gliomas (Table 4) was included. Patient demographics, tumor properties, and sample context are given in Table 5. In reference to the reported normal value cutoffs proposed above, serum levels of R-2-hg were increased in sera from 2 out of 3 patients with actively growing IDHmut tumors (001, 002, and 005). Three other patients, 003, 007, and 010 also had IDHmut tumors but either had shrinking or stable tumors. Surprisingly, the S-2-hg level was increased in a number of samples (003, 006, 008, 010, and 011) and no correlation between IDHmut status or any other variable in Table 5 could explain the observed increase. It is unclear at this point why S-2-hg was increased. Tumor hypoxia, treatment with chemotherapy, or another other, yet unidentified mechanism could be the causative agents for this observation.

TABLE 4

Serum levels of R-2-hg, S-2-hg, Total 2-hg, and 2-hg Ratio for a pilot study of 11 patients. All values shown are reported in μM. Bold denotes increase above proposed cutoff.

| Patient | R-2-hg | S-2-hg | Total 2-hg | 2-hg Ratio |
|---|---|---|---|---|
| 001 | 2.94 | 1.24 | 4.18 | 2.37 |
| 002 | 4.39 | 1.92 | 6.31 | 2.28 |
| 003 | 2.09 | 4.01 | 6.09 | 0.52 |
| 004 | 1.40 | 2.08 | 3.48 | 0.67 |
| 005 | 1.16 | 1.23 | 2.39 | 0.94 |
| 006 | 1.23 | 5.76 | 6.99 | 0.21 |
| 007 | 0.68 | 1.46 | 2.14 | 0.47 |
| 008 | 1.19 | 2.69 | 3.88 | 0.44 |
| 009 | 1.58 | 2.26 | 3.84 | 0.70 |
| 010 | 0.87 | 4.14 | 5.01 | 0.21 |
| 011 | 2.34 | 4.36 | 6.69 | 0.54 |

The importance of distinguishing between each enantiomer is exemplified in the levels of total 2-hg measured across all 11 patients. Those with increased total 2-hg levels included some of those with increased levels of either R-2-hg or S-2-hg, but not all patients with an increase in one enantiomer level, such as patient 001 and patient 008, demonstrated an increase in total 2-hg levels. This shows that measuring total 2-hg alone is useful and that the source of any observed increase in 2-hg could come from either enantiomer. Furthermore, reporting only the 2-hg ratio, can mask any increase in R-2-hg as a potentially large increase in S-2-hg, such as the levels shown from patient 006, could hypothetically cause the ratio to be normal which could mask any subtle, yet significant increase in R-2-hg. Furthermore, using the proposed cutoff for the 2-hg ratio showed no sample with an increase in the R-2-hg: S-2-hg ratio. Lastly, when using race specific cutoffs for 9 of the 11 patients (two were of Asian race), a number of measured levels were marked as an increase (Table 6). For example, the patients 001 and 002 with actively growing IDH mutant tumors now have an increase in their 2-hg ratio, and the Hispanic patient, patient 009, has an increase in S-2-hg and total 2-hg levels. Interestingly, with the race cutoff correction, 6 of the seven who received prior radiation therapy had an increase in S-2-hg (003, 006, 008, 009, 010, 011). In conclusion, three results support taking into account race when determining an individual's normal levels of 2-hg enantiomers.

TABLE 5

Pilot study patient demographics, tumor properties, and sample collection context.

| Patient | Age (yrs.) | Race | Tumor Type | Tumor Grade | IDH Status | Tumor Stability | Sample Context |
|---|---|---|---|---|---|---|---|
| 001 | 32 | C | A | II | Mut | TP | No resection, During TMZ |
| 002 | 57 | C | A/O | III | Mut | TP | Surveillance |
| 003 | 30 | C | A | II | Mut | Shrinking | Post-GTR/XRT During TMZ |
| 004 | 54 | Asian | A | IV | WT | No Tumor | Post-GTR/XRT + TMZ During CCNU + Optune |
| 005 | 40 | Asian | A | IV | Mut | TP | Surveillance |
| 006 | 56 | C | A | IV | WT | TP | Post-STR/XRT/TMZ |
| 007 | 40 | C | A | III | Mut | Stable | During CCNU + Eflornithine |
| 008 | 64 | C | A | IV | WT | Stable | Post-GTR/XRT/TMZ During Optune |
| 009 | 54 | H | A | III | WT | No Tumor | Post-GTR/XRT/TMZ During Optune |
| 010 | 64 | C | A | III | Mut | No Tumor | Post-STR/XRT/TMZ |
| 011 | 60 | C | A | IV | WT | TP | Post-STR/XRT + TMZ/TMZ |

C = Caucasian,
H = Hispanic;
A = astrocytoma,
A/O = anaplastic oligodendroglioma;
GTR = gross total resection,
STR = sub-total resection,
XRT = radiation therapy,
TMZ = temozolomide,
CCNU = lomustine;
TP = tumor progression

TABLE 6

Serum levels of 2-hg enantiomers for a pilot study of 11 patients using race-specific cutoffs. All values shown are reported in μM. Bold denotes increase above proposed cutoff.

| Patient | R-2-hg | S-2-hg | Total 2-hg | 2-hg Ratio |
|---|---|---|---|---|
| 001 | 2.94 | 1.24 | 4.18 | 2.37 |
| 002 | 4.39 | 1.92 | 6.31 | 2.28 |
| 003 | 2.09 | 4.01 | 6.09 | 0.52 |
| 004 | 1.40 | 2.08 | 3.48 | 0.67 |
| 005 | 1.16 | 1.23 | 2.39 | 0.94 |
| 006 | 1.23 | 5.76 | 6.99 | 0.21 |
| 007 | 0.68 | 1.46 | 2.14 | 0.47 |
| 008 | 1.19 | 2.69 | 3.88 | 0.44 |
| 009 | 1.58 | 2.26 | 3.84 | 0.70 |

TABLE 6-continued

Serum levels of 2-hg enantiomers for a pilot study of 11 patients using race-specific cutoffs. All values shown are reported in µM. Bold denotes increase above proposed cutoff.

| Patient | R-2-hg | S-2-hg | Total 2-hg | 2-hg Ratio |
|---------|--------|--------|------------|------------|
| 010     | 0.87   | 4.14 | 5.01  | 0.21       |
| 011     | 2.34   | 4.36 | 6.69  | 0.54       |

As the role of R-2-hg or R-2-hg:S-2-hg as a clinically significant biomarker becomes further defined, there will be a need for reliable and clinically feasible methodologies to separate and detect R-2-hg and S-2-hg enantiomers. The GC-MS/MS assay presented herein demonstrates an efficient and reproducible methodology that has the ability to distinguish 2-hg enantiomers in serum. These data highlight the importance of race and age in the development of normal values in order to interpret 2-hg levels appropriately. Furthermore, the present invention demonstrates the applicability the assay in patients with clinical disease. It is shown that an increase in R-2-hg levels in patients with actively growing disease.

It is contemplated that any embodiment discussed in this specification can be implemented with respect to any method, kit, reagent, or composition of the invention, and vice versa. Furthermore, compositions of the invention can be used to achieve methods of the invention.

It will be understood that particular embodiments described herein are shown by way of illustration and not as limitations of the invention. The principal features of this invention can be employed in various embodiments without departing from the scope of the invention. Those skilled in the art will recognize, or be able to ascertain using no more than routine experimentation, numerous equivalents to the specific procedures described herein. Such equivalents are considered to be within the scope of this invention and are covered by the claims.

All publications and patent applications mentioned in the specification are indicative of the level of skill of those skilled in the art to which this invention pertains. All publications and patent applications are herein incorporated by reference to the same extent as if each individual publication or patent application was specifically and individually indicated to be incorporated by reference.

The use of the word "a" or "an" when used in conjunction with the term "comprising" in the claims and/or the specification may mean "one," but it is also consistent with the meaning of "one or more," "at least one," and "one or more than one." The use of the term "or" in the claims is used to mean "and/or" unless explicitly indicated to refer to alternatives only or the alternatives are mutually exclusive, although the disclosure supports a definition that refers to only alternatives and "and/or." Throughout this application, the term "about" is used to indicate that a value includes the inherent variation of error for the device, the method being employed to determine the value, or the variation that exists among the study subjects.

As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited features, elements, components, groups, integers, and/or steps, but do not exclude the presence of other unstated features, elements, components, groups, integers and/or steps. In embodiments of any of the compositions and methods provided herein, "comprising" may be replaced with "consisting essentially of" or "consisting of". As used herein, the term "consisting" is used to indicate the presence of the recited integer (e.g., a feature, an element, a characteristic, a property, a method/process step or a limitation) or group of integers (e.g., feature(s), element(s), characteristic(s), property(ies), method/process steps or limitation(s)) only. As used herein, the phrase "consisting essentially of" requires the specified features, elements, components, groups, integers, and/or steps, but do not exclude the presence of other unstated features, elements, components, groups, integers and/or steps as well as those that do not materially affect the basic and novel characteristic(s) and/or function of the claimed invention.

The term "or combinations thereof" as used herein refers to all permutations and combinations of the listed items preceding the term. For example, "A, B, C, or combinations thereof" is intended to include at least one of: A, B, C, AB, AC, BC, or ABC, and if order is important in a particular context, also BA, CA, CB, CBA, BCA, ACB, BAC, or CAB. Continuing with this example, expressly included are combinations that contain repeats of one or more item or term, such as BB, AAA, AB, BBC, AAABCCCC, CBBAAA, CABABB, and so forth. The skilled artisan will understand that typically there is no limit on the number of items or terms in any combination, unless otherwise apparent from the context.

As used herein, words of approximation such as, without limitation, "about", "substantial" or "substantially" refers to a condition that when so modified is understood to not necessarily be absolute or perfect but would be considered close enough to those of ordinary skill in the art to warrant designating the condition as being present. The extent to which the description may vary will depend on how great a change can be instituted and still have one of ordinary skill in the art recognize the modified feature as still having the required characteristics and capabilities of the unmodified feature. In general, but subject to the preceding discussion, a numerical value herein that is modified by a word of approximation such as "about" may vary from the stated value by at least ±1, 2, 3, 4, 5, 6, 7, 10, 12 or 15%.

All of the compositions and/or methods disclosed and claimed herein can be made and executed without undue experimentation in light of the present disclosure. While the compositions and methods of this invention have been described in terms of preferred embodiments, it will be apparent to those of skill in the art that variations may be applied to the compositions and/or methods and in the steps or in the sequence of steps of the method described herein without departing from the concept, spirit and scope of the invention. All such similar substitutes and modifications apparent to those skilled in the art are deemed to be within the spirit, scope and concept of the invention as defined by the appended claims.

To aid the Patent Office, and any readers of any patent issued on this application in interpreting the claims appended hereto, applicants wish to note that they do not intend any of the appended claims to invoke paragraph 6 of 35 U.S.C. § 112, U.S.C. § 112 paragraph (f), or equivalent, as it exists on the date of filing hereof unless the words "means for" or "step for" are explicitly used in the particular claim.

For each of the claims, each dependent claim can depend both from the independent claim and from each of the prior dependent claims for each and every claim so long as the prior claim provides a proper antecedent basis for a claim term or element.

REFERENCES

[1] D. Ye, K.-L. Guan, Y. Xiong, Metabolism, Activity, and Targeting of D- and L-2-Hydroxyglutarates., Trends in Cancer. 4 (2018) 151-165. doi:10.1016/j.trecan.2017.12.005.

[2] L. Dang, D. W. White, S. Gross, B. D. Bennett, M. A. Bittinger, E. M. Driggers, V. R. Fantin, H. G. Jang, S. Jin, M. C. Keenan, K. M. Marks, R. M. Prins, P. S. Ward, K. E. Yen, L. M. Liau, J. D. Rabinowitz, L. C. Cantley, C. B. Thompson, M. G. Vander Heiden, S. M. Su, Cancer-associated IDH1 mutations produce 2-hydroxyglutarate, Nature. 462 (2009) 739-744. doi:10.1038/nature08617.

[3] S. Gross, R. A. Cairns, M. D. Minden, E. M. Driggers, M. A. Bittinger, H. G. Jang, M. Sasaki, S. Jin, D. P. Schenkein, S. M. Su, L. Dang, V. R. Fantin, T. W. Mak, Cancer-associated metabolite 2-hydroxyglutarate accumulates in acute myelogenous leukemia with isocitrate dehydrogenase 1 and 2 mutations, J. Exp. Med. 207 (2010).

[4] J. A. Losman, W. G. Kaelin, What a difference a hydroxyl makes: Mutant IDH, (R)-2-hydroxyglutarate, and cancer, Genes Dev. 27 (2013) 836-852. doi:10.1101/gad.217406.113.

[5] H. Sharma, Development of Novel Therapeutics Targeting Isocitrate Dehydrogenase Mutations in Cancer, Curr. Top. Med. Chem. 18 (2018) 505-524. doi:10.2174/1568026618666180518091144.

[6] R. Rzem, M.-F. Vincent, E. Van Schaftingen, M. Veiga-da-Cunha, 1-2-Hydroxyglutaric aciduria, a defect of metabolite repair, J. Inherit. Metab. Dis. 30 (2007) 681-689. doi:10.1007/s10545-007-0487-0.

[7] E. A. Struys, 2-Hydroxyglutarate is not a metabolite; D-2-hydroxyglutarate and L-2-hydroxyglutarate are!, PNAS. 110 (2013) E4939. doi:10.1073/pnas.1318777110.

[8] P. A. Tyrakis, A. Palazon, D. Macias, K. L. Lee, A. T. Phan, P. Veliça, J. You, G. S. Chia, J. Sim, A. Doedens, A. Abelanet, C. E. Evans, J. R. Griffiths, L. Poellinger, A. W. Goldrath, R. S. Johnson, S-2-hydroxyglutarate regulates CD8+T-lymphocyte fate, Nature. 540 (2016) 236-241. doi:10.1038/nature20165.

[9] A. J. Worth, K. P. Gillespie, C. Mesaros, L. Guo, S. S. Basu, N. W. Snyder, I. A. Blair, Rotenone Stereospecifically Increases (S)-2-Hydroxyglutarate in SH-SY5Y Neuronal Cells, Chem. Res. Toxicol. 28 (2015) 948-954. doi:10.1021/tx500535c.

[10] M. Kranendijk, E. A. Struys, G. S. Salomons, M. S. Van der Knaap, C. Jakobs, Progress in understanding 2-hydroxyglutaric acidurias, J. Inherit. Metab. Dis. 35 (2012) 571-587. doi:10.1007/s10545-012-9462-5.

[11] A. Intlekofer, R. Dematteo, S. Venneti, L. S. Finley, C. Lu, A. Judkins, A. Rustenburg, P. Grinaway, J. Chodera, J. Cross, C. Thompson, Hypoxia Induces Production of L-2-Hydroxyglutarate, Cell Metab. 22 (2015) 304-311. doi:10.1016/j.cmet.2015.06.023.

[12] J. P. Kamerling, G. J. Gerwig, J. F. Vliegenthart, Determination of the configurations of lactic and glyceric acids from human serum and urine by capillary gas-liquid chromatography., J. Chromatogr. 143 (1977) 117-23. http://www.ncbi.nlm.nih.gov/pubmed/838825 (accessed Sep. 19, 2018).

[13] J. P. Kamerling, M. Duran, G. J. Gerwig, D. Ketting, L. Bruinvis, J. F. G. Vliegenthart, S. K. Wadman, Determination of the absolute configuration of some biologically important urinary 2-hydroxydicarboxylic acids by capillary gas-liquid chromatography, J. Chromatogr. B Biomed. Sci. Appl. 222 (1981) 276-283. doi:10.1016/50378-4347(00)81061-0.

[14] R. A. Chalmers, A. M. Lawson, R. W. E. Watts, A. S. Tavill, J. P. Kamerling, E. Hey, D. Ogilvie, D-2-hydroxyglutaric aciduria: Case report and biochemical studies, J. Inherit. Metab. Dis. 3 (1980) 11-15. doi:10.1007/BF02312516.

[15] O. van Tellingen, B. Yetkin-Arik, M. C. de Gooijer, P. Wesseling, T. Wurdinger, H. E. de Vries, Overcoming the blood-brain tumor barrier for effective glioblastoma treatment, Drug Resist. Updat. 19 (2015) 1-12. doi:10.1016/J.DRUP.2015.02.002.

[16] E. A. Struys, E. E. W. Jansen, N. M. Verhoeven, C. Jakobs, Measurement of urinary D- and L-2-hydroxyglutarate enantiomers by stable-isotope-dilution liquid chromatography-tandem mass spectrometry after derivatization with diacetyl-L-tartaric anhydride., Clin. Chem. 50 (2004) 1391-5. doi:10.1373/clinchem.2004.033399.

[17] Q.-Y. Cheng, J. Xiong, W. Huang, Q. Ma, W. Ci, Y.-Q. Feng, B.-F. Yuan, Sensitive Determination of Onco-metabolites of D- and L-2-hydroxyglutarate Enantiomers by Chiral Derivatization Combined with Liquid Chromatography/Mass Spectrometry Analysis, Sci. Rep. 5 (2015).

[18] M. S. Rashed, M. AlAmoudi, H. Y. Aboul-Enein, Chiral liquid chromatography tandem mass spectrometry in the determination of the configuration of 2-hydroxyglutaric acid in urine, Biomed. Chromatogr. 14 (2000) 317-320. doi:10.1002/1099-0801(200008)14:5<317::AID-BMC989>3.0.CO;2-V.

[19] C. Calderón, J. Horak, M. Lämmerhofer, Chiral separation of 2-hydroxyglutaric acid on cinchonan carbamate based weak chiral anion exchangers by high-performance liquid chromatography, J. Chromatogr. A. 1467 (2016) 239-245. doi:10.1016/J.CHROMA.2016.05.042.

[20] C. Calderón, M. Lämmerhofer, Chiral separation of short chain aliphatic hydroxycarboxylic acids on cinchonan carbamate-based weak chiral anion exchangers and zwitterionic chiral ion exchangers, J. Chromatogr. A. 1487 (2017) 194-200. doi:10.1016/J.CHROMA.2017.01.060.

[21] R. A. Patil, C. A. Weatherly, D. W. Armstrong, Chiral Gas Chromatography, Chiral Anal. (2018) 468-505. doi:10.1016/B978-0-444-64027-7.00012-4.

[22] C. D. DiNardo, K. J. Propert, A. W. Loren, E. Paietta, Z. Sun, R. L. Levine, K. S. Straley, K. Yen, J. P. Patel, S. Agresta, O. Abdel-Wahab, A. E. Perl, M. R. Litzow, J. M. Rowe, H. M. Lazarus, H. F. Fernandez, D. J. Margolis, M. S. Tallman, S. M. Luger, M. Carroll, Serum 2-hydroxyglutarate levels predict isocitrate dehydrogenase mutations and clinical outcome in acute myeloid leukemia, Blood. 121 (2013).

[23] J.-H. Wang, W.-L. Chen, J.-M. Li, S.-F. Wu, T.-L. Chen, Y.-M. Zhu, W.-N. Zhang, Y. Li, Y.-P. Qiu, A.-H. Zhao, J.-Q. Mi, J. Jin, Y.-G. Wang, Q.-L. Ma, H. Huang, D.-P. Wu, Q.-R. Wang, Y. Li, X.-J. Yan, J.-S. Yan, J.-Y. Li, S. Wang, X.-J. Huang, B.-S. Wang, W. Jia, Y. Shen, Z. Chen, S.-J. Chen, Prognostic significance of 2-hydroxyglutarate levels in acute myeloid leukemia in China., Proc. Natl. Acad. Sci. U.S.A 110 (2013) 17017-22. doi:10.1073/pnas.1315558110.

[24] M. Janin, E. Mylonas, V. Saada, J.-B. Micol, A. Renneville, C. Quivoron, S. Koscielny, L. Scourzic, S. Forget, C. Pautas, D. Caillot, C. Preudhomme, H. Dombret, C. Berthon, R. Barouki, D. Rabier, N. Auger, F. Griscelli, E. Chachaty, E. Leclercq, M.-H. Courtier, A. Bennaceur-Griscelli, E. Solary, O. A. Bernard, V. Penard-Lacronique, C. Ottolenghi, S. de Botton, Serum 2-Hydroxyglutarate Production in IDH1- and IDH2-Mutated De Novo Acute Myeloid Leukemia: A Study by the Acute Leukemia French Association Group, J. Clin. Oncol. 32 (2014) 297-305. doi:10.1200/JCO.2013.50.2047.

[25] J. Balss, C. Thiede, T. Bochtler, J. G. Okun, M. Saadati, A. Benner, S. Pusch, G. Ehninger, M. Schaich, A. D. Ho, A. von Deimling, A. Krämer, C. E. Heilig, Pretreatment d-2-hydroxyglutarate serum levels negatively impact on outcome in IDH1-mutated acute myeloid leukemia, Leukemia. 30 (2016) 782-788. doi:10.1038/leu.2015.317.

[26] J. Delahousse, L. Verlingue, S. Broutin, C. Legoupil, M. Touat, L. Doucet, S. Ammari, L. Lacroix, M. Ducreux, J.-Y. Scoazec, D. Malka, A. Paci, A. Hollebecque, Circulating oncometabolite D-2-hydroxyglutarate enantiomer is a surrogate marker of isocitrate dehydrogenase-mutated intrahepatic cholangiocarcinomas, Eur. J. Cancer. 90 (2018) 83-91. doi:10.1016/J.EJCA.2017.11.024.

[27] P. M. Jones, R. Boriack, E. A. Struys, D. Rakheja, Measurement of Oncometabolites d-2-Hydroxyglutaric Acid and 1-2-Hydroxyglutaric Acid, in: Humana Press, New York, N.Y., 2017: pp. 219-234. doi:10.1007/978-1-4939-7142-8_14.

[28] H. Churchill, H. Naina, R. Boriack, D. Rakheja, W. Chen, Discordant intracellular and plasma D-2-hydroxyglutarate levels in a patient with IDH2 mutated angioimmunoblastic T-cell lymphoma, Int. J. Clin. Exp. Pathol. 8 (2015) 11753-9. http://www.ncbi.nlm.nih.gov/pubmed/26617922 (accessed Oct. 11, 2018).

[29] D. Rakheja, F. Fuda, T. Vandergriff, R. Boriack, B. C. Medeiros, A. E. Frankel, W. Chen, Increased plasma d-2-hydroxyglutarate in isocitrate dehydrogenase 2-mutated blastic plasmacytoid dendritic cell neoplasm, Hum. Pathol. 46 (2015) 322-326. doi:10.1016/J.HUMPATH.2014.10.013.

[30] M. Seijo-Martinez, C. Navarro, M. Castro del Rio, O. Vila, M. Puig, A. Ribes, M. Butron, L-2-Hydroxyglutaric Aciduria, Arch. Neurol. 62 (2005) 666. doi:10.1001/archneur.62.4.666.

[31] D. S. Wishart, Y. D. Feunang, A. Marcu, A. C. Guo, K. Liang, R. Vazquez-Fresno, T. Sajed, D. Johnson, C. Li, N. Karu, Z. Sayeeda, E. Lo, N. Assempour, M. Berjanskii, S. Singhal, D. Arndt, Y. Liang, H. Badran, J. Grant, A. Serra-Cayuela, Y. Liu, R. Mandal, V. Neveu, A. Pon, C. Knox, M. Wilson, C. Manach, A. Scalbert, HMDB 4.0: the human metabolome database for 2018, Nucleic Acids Res. 46 (2018) D608-D617. doi:10.1093/nar/gkx1089.

[32] K. M. Gibson, H. J. Ten Brink, D. S. M. Schor, R. M. Kok, A. H. Bootsma, G. F. Hoffmann, C. Jakobs, Stable-Isotope Dilution Analysis of D- and L-2-Hydroxyglutaric Acid: Application to the Detection and Prenatal Diagnosis of D- and L-2-Hydroxyglutaric Acidemias, Pediatr. Res. 34 (1993) 277-280. doi:10.1203/00006450-199309000-00007.

[33] G. F. Hoffmann, W. Meier-Augenstein, S. Stockier, R. Surtees, D. Rating, W. L. Nyhan, Physiology and pathophysiology of organic acids in cerebrospinal fluid, J. Inherit. Metab. Dis. 16 (1993) 648-69. http://www.ncbi.nlm.nih.gov/pubmed/8412012 (accessed Oct. 11, 2018).

[34] P.-N. Bories, S. Nakib, L. Cynober, A.-S. Alary, M.-M. Coude, F. Chevillon, J. Tamburini, R. Birsen, O. Kosmider, D. Bouscary, Establishing assay-specific 97.5th percentile upper reference limit for serum D-2-hydroxyglutarate for the management of patients with acute myeloid leukemia, Clin. Chem. Lab. Med. 0 (2018) e57-e59. doi:10.1515/cclm-2018-0427.

[35] J. O. Wobbrock, L. Findlater, D. Gergle, J. J. Higgins, The aligned rank transform for nonparametric factorial analyses using only anova procedures, in: Proc. 2011 Annu. Conf. Hum. Factors Comput. Syst.—CHI'11, ACM Press, New York, N.Y., USA, 2011: p. 143. doi:10.1145/1978942.1978963.

[36] M. Duran, J. P. Kamerling, H. D. Bakker, A. H. van Gennip, S. K. Wadman, L-2-Hydroxyglutaric aciduria: an inborn error of metabolism?, J. Inherit. Metab. Dis. 3 (1980) 109-12. http://www.ncbi.nlm.nih.gov/pubmed/6787330 (accessed Oct. 16, 2018).

[37] J. P. Kamerling, G. J. Gerwig, J. F. Vliegenthart, Determination of the configurations of lactic and glyceric acids from human serum and urine by capillary gas-liquid chromatography, J. Chromatogr. 143 (1977) 117-23. http://www.ncbi.nlm.nih.gov/pubmed/838825 (accessed Oct. 29, 2018).

[38] J. P. Kamerling, M. Duran, G. J. Gerwig, D. Ketting, L. Bruinvis, J. F. G. Vliegenthart, S. K. Wadman, Determination of the absolute configuration of some biologically important urinary 2-hydroxydicarboxylic acids by capillary gas-liquid chromatography, J. Chromatogr. B Biomed. Sci. Appl. 222 (1981) 276-283. doi:10.1016/S0378-4347(00)81061-0.

[39] F. Sahm, D. Capper, S. Pusch, J. Balss, A. Koch, C.-D. Langhans, J. G. Okun, A. von Deimling, Detection of 2-Hydroxyglutarate in Formalin-Fixed Paraffin-Embedded Glioma Specimens by Gas Chromatography/Mass Spectrometry, Brain Pathol. 22 (2012) 26-31. doi:10.1111/j.1750-3639.2011.00506.x.

[40] F. and D. A. FDA, Bioanalytical method validation: Guidance for Industry, 2018. https://www.fda.gov/Drugs/GuidanceComplianceRegulatoryInformation/Guidances/default.htm.

[41] C. Willekens, J.-B. Micol, V. Poinsignon, C. Quivoron, V. Saada, S. Broutin, M. Terroir-Cassou-Mounat, D. Ghez, J.-H. Bourhis, J. Bosq, V. Ribrag, A. Paci, V. Lacronique-Penard, S. De Botton, Serum 2-Hydroxyglutarate Level Can Predict IDH2 Mutation in Myeloid Sarcoma, Blood. 126 (2015). http://www.bloodjournal.org/content/126/23/3835?sso-checked=true (accessed Oct. 11, 2018).

[42] M. Kranendijk, E. A. Struys, G. S. Salomons, M. S. Van der Knaap, C. Jakobs, Progress in understanding 2-hydroxyglutaric acidurias, J. Inherit. Metab. Dis. 35 (2012) 571-87. doi:10.1007/s10545-012-9462-5.

[43] D. Capper, M. Simon, C.-D. Langhans, J. G. Okun, J. C. Tonn, M. Weller, A. von Deimling, C. Hartmann, 2-Hydroxyglutarate concentration in serum from patients with gliomas does not correlate with IDH1/2 mutation status or tumor size, Int. J. Cancer. 131 (2012) 766-768. doi:10.1002/ijc.26425.

[44] G. Lombardi, G. Corona, L. Bellu, A. Della Puppa, A. Pambuku, P. Fiduccia, R. Bertorelle, M. P. Gardiman, D. D'Avella, G. Toffoli, V. Zagonel, Diagnostic value of plasma and urinary 2-hydroxyglutarate to identify patients with isocitrate dehydrogenase-mutated glioma, Oncologist. 20 (2015) 562-7. doi:10.1634/theoncologist.2014-0266.

[45] D. R. Borger, L. Goyal, T. Yau, R. T. Poon, M. Ancukiewicz, V. Deshpande, D. C. Christiani, H. M. Liebman, H. Yang, H. Kim, K. Yen, J. E. Faris, A. J. Iafrate, E. L. Kwak, J. W. Clark, J. N. Allen, L. S. Blaszkowsky, J. E. Murphy, S. K. Saha, T. S. Hong, J. Y.

Wo, C. R. Ferrone, K. K. Tanabe, N. Bardeesy, K. S. Straley, S. Agresta, D. P. Schenkein, L. W. Ellisen, D. P. Ryan, A. X. Zhu, Circulating Oncometabolite 2-Hydroxyglutarate Is a Potential Surrogate Biomarker in Patients with Isocitrate Dehydrogenase-Mutant Intrahepatic Cholangiocarcinoma, Clin. Cancer Res. 20 (2014).

[46] A. M. Brunner, D. S. Neuberg, S. A. Wander, H. Sadrzadeh, K. K. Ballen, P. C. Amrein, G. S. Hobbs, Y.-B. Chen, A. M. Perry, C. Joseph, M. E. Burke, A. Y. Ramos, R. Silver, I. Galinsky, S. Adamia, D. Borger, A. J. Iafrate, R. M. Stone, A. T. Fathi, Use of 2HG Levels in the Serum, Urine, or Bone Marrow to Predict IDH Mutations in Adults with Acute Myeloid Leukemia, Blood. 126 (2015). http://www.bloodjournal.org/content/126/23/2597?sso-checked=true (accessed Oct. 11, 2018).

[47] M. Y. Eng, S. E. Luczak, T. L. Wall, ALDH2, ADH1B, and ADH1C genotypes in Asians: a literature review, Alcohol Res. Health. 30 (2007) 22-7. http://www.ncbi.nlm.nih.gov/pubmed/17718397 (accessed Oct. 30, 2018).

[48] C. Franceschi, J. Campisi, Chronic Inflammation (Inflammaging) and Its Potential Contribution to Age-Associated Diseases, Journals Gerontol. Ser. A Biol. Sci. Med. Sci. 69 (2014) S4-S9. doi:10.1093/gerona/glu057.

[49] D. Senyilmaz, A. A. Teleman, Chicken or the egg: Warburg effect and mitochondrial dysfunction, F1000Prime Rep. 7 (2015) 41. doi:10.12703/P7-41.

[50] J. Han, D. Jackson, J. Holm, K. Turner, P. Ashcraft, X. Wang, B. Cook, E. Arning, R. M. Genta, K. Venuprasad, R. F. Souza, L. Sweetman, A. L. Theiss, Elevated d-2-hydroxyglutarate during colitis drives progression to colorectal cancer, Proc. Natl. Acad. Sci. U.S.A 115 (2018) 1057-1062. doi:10.1073/pnas.1712625115.

[51] A. L. Cohen, S. L. Holmen, H. Colman, IDH1 and IDH2 Mutations in Gliomas, Curr. Neurol. Neurosci. Rep. 13 (2013) 345. doi:10.1007/s11910-013-0345-4.

What is claimed is:

1. A method of identifying 2-hydroxygluterate (2-hg) metabolites in a sample comprising:
   a) obtaining the sample from a patient, wherein the biological fluid is selected from at least one of: serum, urine, cerebrospinal fluid, or sputum;
   b) extracting the 2-hydroxygluterate (2-hg) metabolites from the sample;
   c) derivatizing the 2-hydroxygluterate (2-hg) metabolites with trimethylsilyldiazomethane (TMSDAM) and methanol;
   d) separating the one or more 2-hg metabolites in the sample using a chiral gas chromatography capillary column; and
   e) quantitating an amount of 2-hg metabolites and enantiomers in the sample using mass spectrometry (MS).

2. The method of claim 1, wherein the 2-hg metabolites are (R)-2-hydroxygluterate ((R)-2-hg) and (S)-2-hydroxygluterate ((S)-2-hg).

3. The method of claim 1, wherein the 2-hg metabolites are quantitated without at least one of: a second extraction step, a centrifugation step, or an incubation step.

4. The method of claim 1, wherein the mass spectrometry is selected from MS/MS, MS/MS fragmentation followed by Gas Chromatograph, or triple quadrupole MS.

* * * * *